United States Patent
Stigall et al.

(10) Patent No.: US 11,413,017 B2
(45) Date of Patent: Aug. 16, 2022

(54) PRE-DOPED SOLID SUBSTRATE FOR INTRAVASCULAR DEVICES

(71) Applicant: Koninklijke Philips N.V., Amsterdam (NL)

(72) Inventors: Jeremy Stigall, Carlsbad, CA (US); Maritess Minas, San Diego, CA (US); Gloria Robinson, San Diego, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 495 days.

(21) Appl. No.: 14/694,547

(22) Filed: Apr. 23, 2015

(65) Prior Publication Data

US 2015/0305710 A1 Oct. 29, 2015

Related U.S. Application Data

(60) Provisional application No. 61/985,220, filed on Apr. 28, 2014.

(51) Int. Cl.
| | | |
|---|---|---|
| *A61B 8/00* | (2006.01) | |
| *A61B 8/12* | (2006.01) | |
| *A61B 8/08* | (2006.01) | |
| *B06B 1/06* | (2006.01) | |
| *G10K 11/00* | (2006.01) | |

(52) U.S. Cl.
CPC ............ *A61B 8/445* (2013.01); *A61B 8/0891* (2013.01); *A61B 8/12* (2013.01); *A61B 8/4494* (2013.01); *B06B 1/0685* (2013.01); *G10K 11/002* (2013.01)

(58) Field of Classification Search
CPC .......... A61B 8/445; A61B 8/4494; A61B 8/12; A61B 8/0891; A61B 8/44; A61B 8/4444; A61B 8/4483; B06B 1/0685; B06B 1/0681
See application file for complete search history.

(56) References Cited

U.S. PATENT DOCUMENTS

| | | | | |
|---|---|---|---|---|
| 5,188,106 | A * | 2/1993 | Nappholz | A61B 8/065 128/DIG. 13 |
| 5,363,853 | A | 11/1994 | Lieber | |
| 5,531,700 | A | 7/1996 | Yue-Teh et al. | |
| 5,648,941 | A | 7/1997 | King | |
| 6,049,958 | A * | 4/2000 | Eberle | A61B 1/0011 29/25.35 |

(Continued)

FOREIGN PATENT DOCUMENTS

| | | |
|---|---|---|
| EP | 0388112 | 9/1990 |
| EP | 1608422 | 1/2013 |

OTHER PUBLICATIONS

Epoxy (www.epoxy-europe.eu/epoxies/how-are-epoxies-made/, retrieved Dec. 23, 2021).*

(Continued)

*Primary Examiner* — Carolyn A Pehlke

(57) ABSTRACT

Systems, devices, and methods provide a solid-state intravascular ultrasound (IVUS) imaging system that includes an array of ultrasound transducers mounted on a structural uni-body made of a polymeric substance doped with acoustic dampening material. The use of the polymeric substance doped with acoustic dampening material to fabricate the uni-body assists in improving the signal-to-noise ratio associated with the IVUS imaging signals.

20 Claims, 8 Drawing Sheets

(56) References Cited

U.S. PATENT DOCUMENTS

| | | | |
|---|---|---|---|
| 6,605,062 B1 | 8/2003 | Chi et al. | |
| 6,641,540 B2 | 11/2003 | Fleischman | |
| 6,776,763 B2 | 8/2004 | Nix | |
| 7,226,418 B2 | 6/2007 | Kim | |
| 2003/0050661 A1 | 3/2003 | Kramer | |
| 2003/0114732 A1* | 6/2003 | Webler | A61B 1/00154 |
| | | | 600/121 |
| 2004/0113524 A1 | 6/2004 | Baumgartner et al. | |
| 2005/0275313 A1 | 12/2005 | Yamashita et al. | |
| 2006/0103265 A1 | 5/2006 | Miyoshi | |
| 2007/0016071 A1 | 1/2007 | Eberle et al. | |
| 2007/0265516 A1 | 11/2007 | Wang | |
| 2009/0036832 A1 | 2/2009 | Skujins | |
| 2009/0118675 A1 | 5/2009 | Czyscon | |
| 2010/0317973 A1* | 12/2010 | Nita | A61B 17/22012 |
| | | | 600/467 |
| 2010/0331697 A1 | 12/2010 | Webler et al. | |
| 2011/0034809 A1 | 2/2011 | Eberle et al. | |
| 2013/0150716 A1 | 6/2013 | Stigall et al. | |
| 2014/0180072 A1* | 6/2014 | Davies | A61B 8/12 |
| | | | 600/424 |
| 2014/0187960 A1* | 7/2014 | Corl | A61B 8/12 |
| | | | 600/466 |

OTHER PUBLICATIONS

Hunter, Tim B., and Mihra S. Taljanovic. "Foreign bodies." Radiographics 23.3 (2003): 731-757.*
Korean Intellectual Property Office, International Search Report for PCT/US2015/027292 dated Jul. 15, 2015, 12 pages.

* cited by examiner

PRE-DOPED SOLID SUBSTRATE FOR INTRAVASCULAR DEVICES

CROSS REFERENCE TO RELATED APPLICATIONS

The present application claims priority to and the benefit of the U.S. Provisional Patent Application No. 61/985,220, filed Apr. 28, 2014, which is hereby incorporated by reference in its entirety.

FILED OF DISCLOSURE

The present disclosure relates generally to improving and optimizing acoustic performance of intravascular ultrasound (IVUS) imaging systems and, in particular, to solid-state IVUS imaging systems. In various embodiments according to the present disclosure, the solid-state IVUS imaging system may include an array of ultrasound transducers that are connected to a flex circuit and mounted on a structural uni-body. The uni-body may be made of a polymeric substance pre-doped with acoustic dampening material. In this way, the signal-to-noise ratio associated with the IVUS imaging signals and, therefore, the overall quality of the IVUS image, may be improved.

BACKGROUND

IVUS imaging systems are widely used in interventional cardiology as a diagnostic tool for assessing a vessel, such as an artery, within the body of the patient to determine the need for treatment, to guide intervention, and/or to assess the effectiveness of administered treatment. Two types of intravascular devices commonly used in IVUS imaging systems are rotational and solid-state. A conventional rotational intravascular device may include a flexible drive cable that continually rotates inside the sheath of the intravascular device inserted into the vessel of interest. On the other hand, a solid-state intravascular device carries an ultrasound scanner assembly that includes an array of ultrasound transducers (typically 32 or 64) distributed around the circumference of the device connected to a set of transducer control circuits. The transducer control circuits select individual or a subset of transducers for transmitting an ultrasound pulse and for receiving the echo signal for imaging. By stepping through a sequence of transmit-receive transducer pairs, the solid-state intravascular device can synthesize the effect of a mechanically scanned transducer element, but without moving parts. Further, because there are no moving parts, the interface is simplified and the scanner assembly can be wired directly to the imaging system with a simple electrical cable.

The transducers in the conventional solid-state intravascular device are typically mounted onto a flex circuit which is wrapped around a stainless steel uni-body. The flex circuit is then sealed onto the stainless steel uni-body. Further, to improve acoustic performance, any cavities between the flex circuit and the surface of the stainless steel uni-body are filled with liquid backing material. The assembly is then cured to allow the liquid backing material to solidify and set. Once set, any excess backing material is cleaned off.

The conventional solid-state intravascular devices fail to ensure high acoustic performance during IVUS imaging. In particular, as discussed above, in the conventional solid-state intravascular devices, the cavities between the flex circuit and the surface of the stainless steel uni-body are filled with the liquid backing material to improve the acoustic performance. However, since the liquid backing material is typically injected through openings measuring 0.007 inches in diameter, air pockets can be formed within the cavities, and this deteriorates the acoustic performance of the solid-state intravascular device. Also, there is no way to ensure consistency in the filling of the different cavities via the injecting of the liquid backing material. Therefore, the acoustic performance is inconsistent and non-uniform when using different predetermined subsets of the transducers. Finally, the assembly must be heated to cure the liquid backing material and then cleaned off to remove any excess backing material, thereby undesirably increasing the time and cost associated with manufacturing the conventional solid-state intravascular device.

As such, there remains a need to improve and optimize the acoustic performance of solid-state IVUS imaging systems while managing the time and cost associated with manufacturing the same. The devices, systems, and methods disclosed herein overcome one or more of the deficiencies of the conventional devices.

SUMMARY

In one aspect, the present disclosure provides a device comprising a scanner assembly that includes a ferrule including a lumen region, a uni-body surrounding at least a portion of the ferrule, the uni-body being made of a polymeric substance doped with acoustic dampening material, and a flex circuit being mounted onto the uni-body, the flex circuit including a transducer array. In some embodiments, the ferrule and the uni-body may be cylindrical in shape. Further, the ferrule may be made of a metallic or a polymer. In some embodiments, the lumen region of the ferrule may be sized and shaped to receive a guide wire. In some embodiments, the acoustic dampening material may be any type of a conductive adhesive, such as epoxy. In some embodiments, the polymeric substance may be uniformly doped with the acoustic dampening material. The flex circuit may be mounted onto the uni-body by wrapping the flex circuit in a rolled configuration around the uni-body. The flex circuit may be fixedly secured to the uni-body with an adhesive. In some embodiments, the uni-body may include a plurality of radiopaque markers. The plurality of radiopaque markers may include separate elements fixedly secured to an outer surface of the uni-body. The uni-body may be doped with a radiopaque material to form the plurality of radiopaque markers. Further, the uni-body may include at least one radiopaque marker on a portion of the uni-body covered by the flex circuit. In some embodiments, the uni-body may include a control region and a transducer region, the control region having a different cross-sectional profile with respect to the transducer region. In some embodiments, the uni-body may include a transition zone which transitions in shape between the control region having a non-circular cross-sectional profile and the transducer region having a circular cross-sectional profile.

In another aspect, the present disclosure provides a method to provide a scanner assembly of an intravascular ultrasound (IVUS) device. The method may include providing a polymeric material doped with acoustic dampening material, fabricating a uni-body with the doped polymeric material, and mounting a flex circuit having a transducer array onto the fabricated uni-body. The mounting the flex circuit may include fixedly securing the flex circuit onto the uni-body using an adhesive. In some embodiments, the fabricating may include swaging the doped polymeric material using a die, injection molding the doped polymeric material, and/or extruding the doped polymeric material. In some embodiments, the providing the uni-body may include uniformly doping the polymeric material with the acoustic dampening material. The method may further include fixedly securing a plurality of radiopaque markers to an outer surface of the uni-body. In some embodiments, the plurality of radiopaque markers may be separate elements. In some embodiments, the uni-body may be doped with radiopaque material to form a plurality of radiopaque markers. In some embodiments, at least one radiopaque marker may be provided on a portion of the uni-body covered by the flex circuit.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship, and dimensions of the parts to form the following embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

The following is a brief description of each figure used to describe the present invention, and thus, is being presented for illustrative purposes only and should not be limitative of the scope of the present invention.

Figure 1:
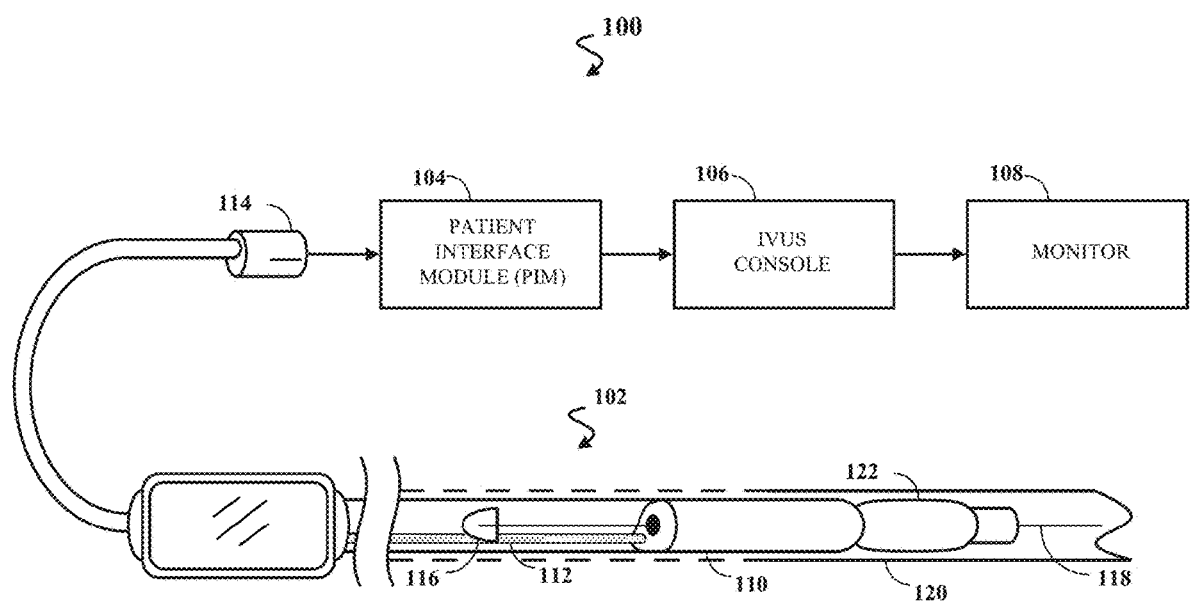

FIG. 1 is a diagrammatic schematic view of an exemplary intravascular ultrasound (IVUS) imaging system according to an embodiment of the present disclosure.

Figure 2:
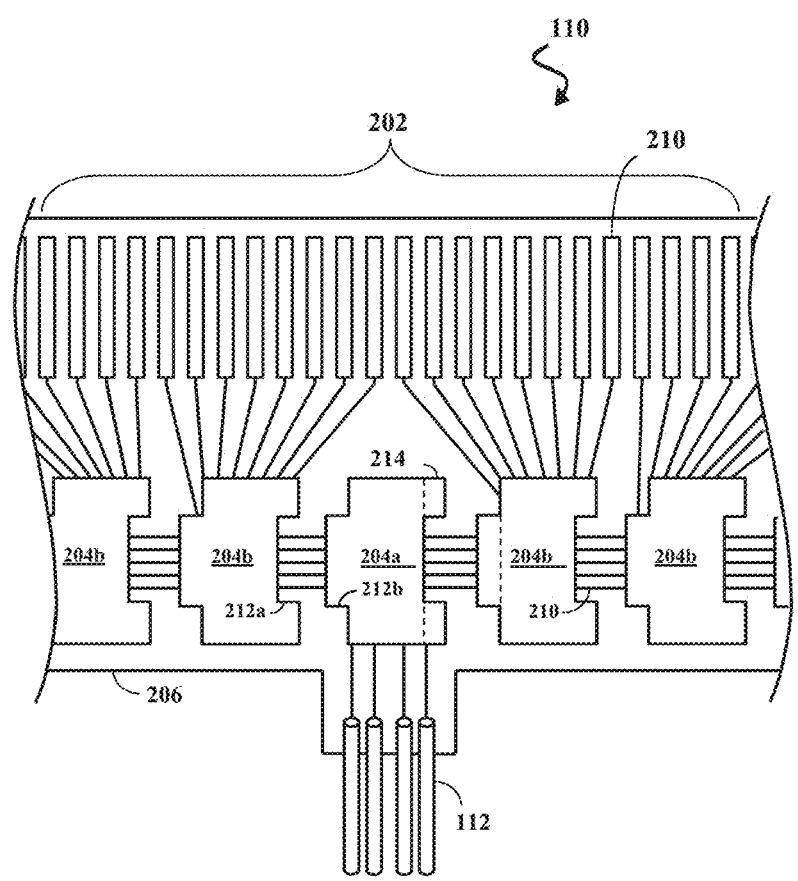

FIG. 2 is a top view of a portion of an exemplary ultrasound scanner assembly according to an embodiment of the present disclosure.

Figure 3:
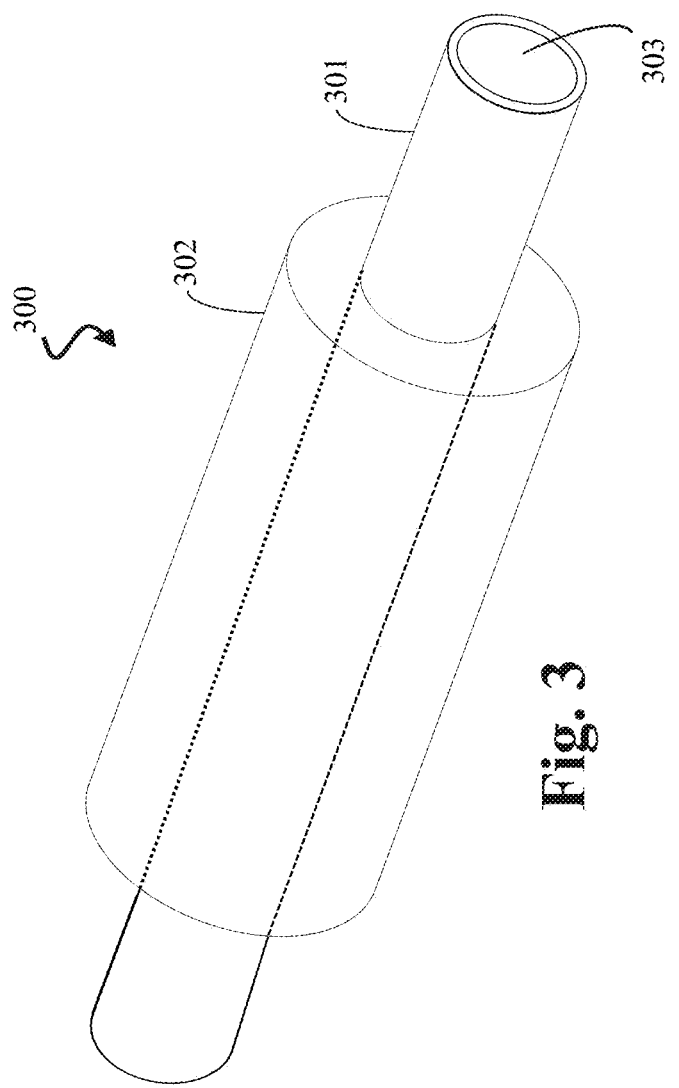

FIG. 3 is a perspective view of an exemplary mounting structure according to an embodiment of the present disclosure.

Figure 4:
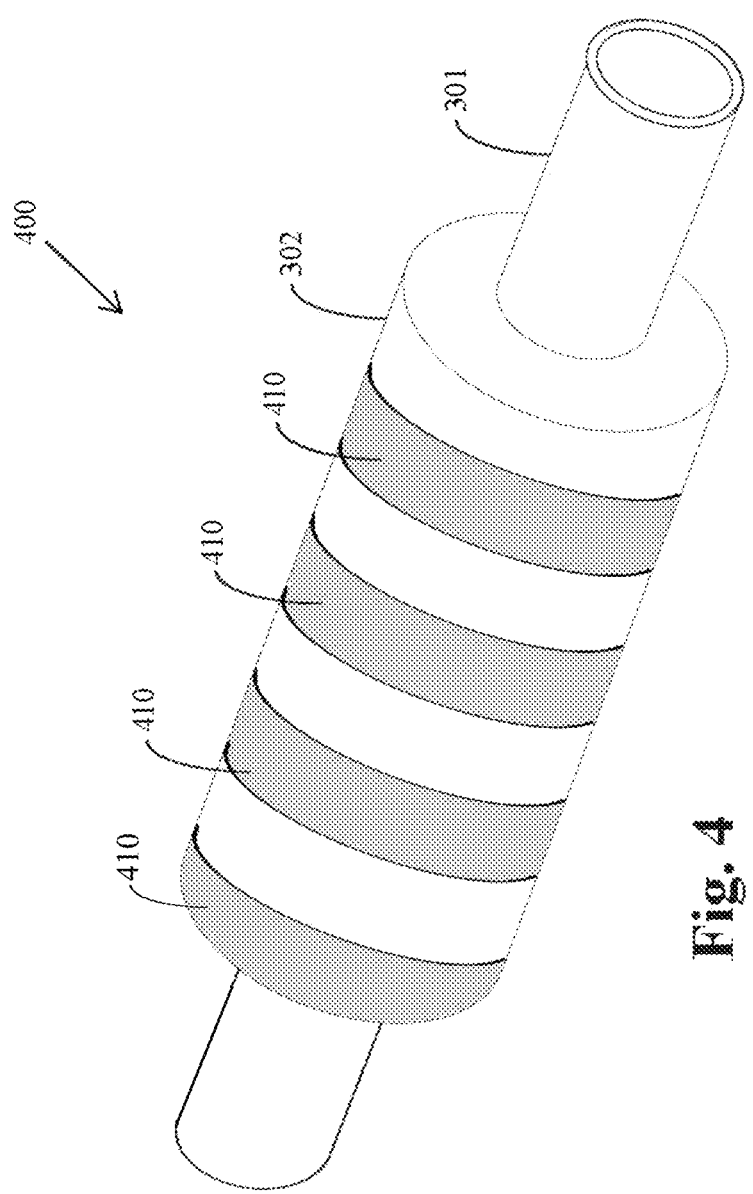

FIG. 4 is a perspective view of exemplary mounting structure according to another embodiment of the present disclosure.

Figure 5:
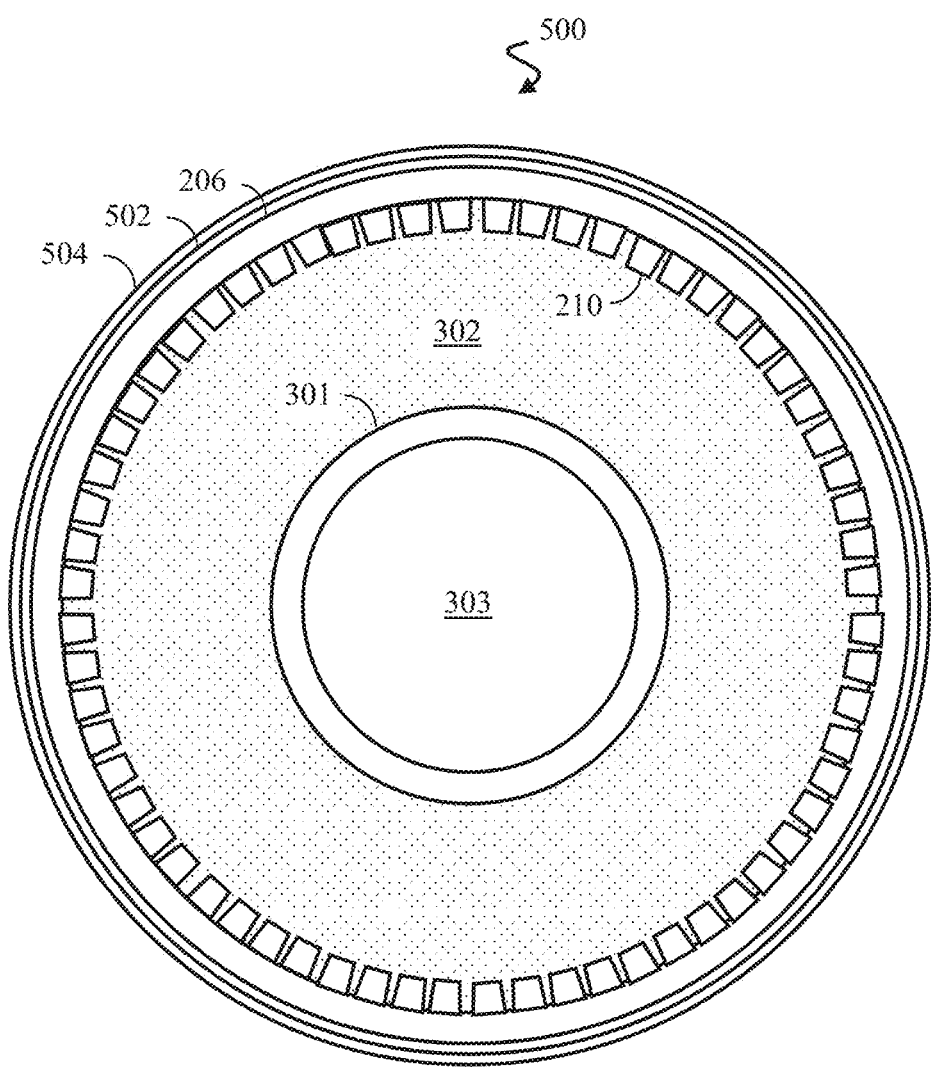

FIG. 5 is a cross-sectional end view of an exemplary transducer region of the ultrasound scanner assembly according to an embodiment of the present disclosure.

Figure 6:
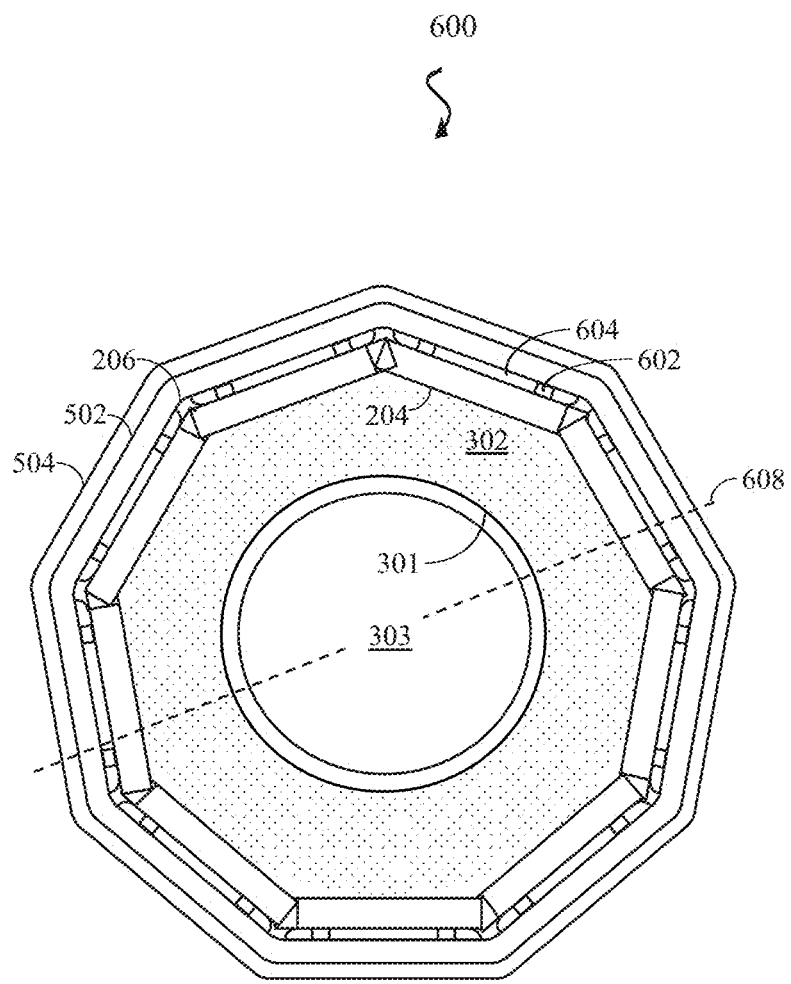

FIG. 6 is a cross-sectional end view of an exemplary control region of the ultrasound scanner assembly according to an embodiment of the present disclosure.

Figure 7:
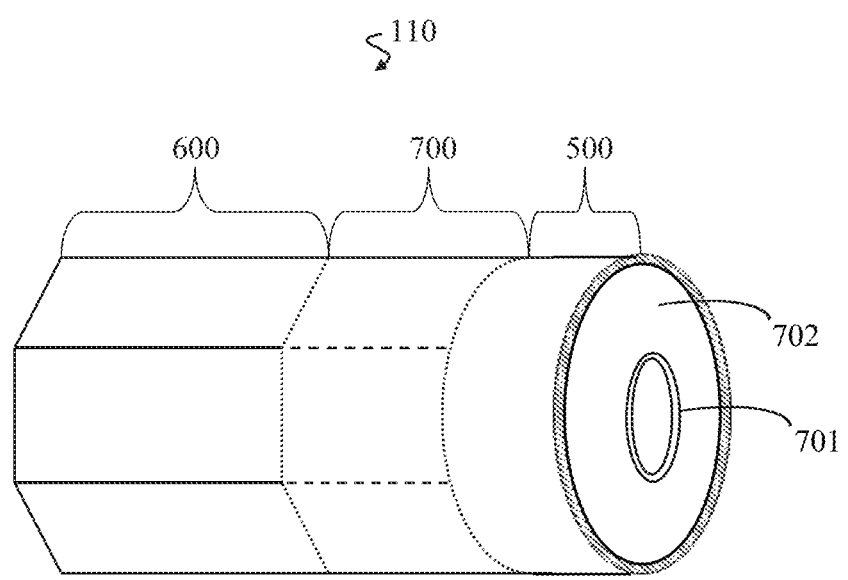

FIG. 7 is a perspective view of a portion of an exemplary ultrasound scanner assembly according to an embodiment of the present disclosure.

Figure 8:
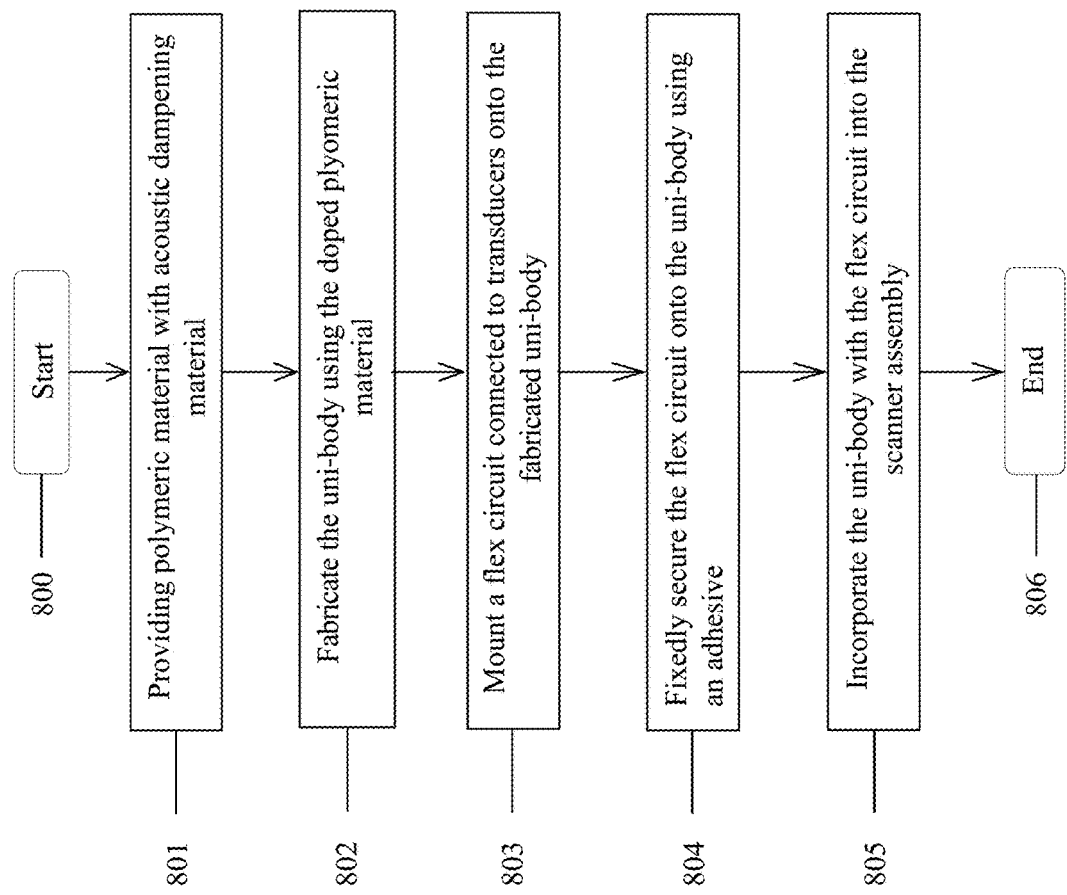

FIG. 8 illustrates an exemplary method to provide a scanner assembly according to an embodiment of the present disclosure.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the IVUS system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As discussed above, there remains a need to improve and optimize the acoustic performance of solid-state IVUS imaging systems. The present disclosure describes devices, systems, and methods to improve and to optimize acoustic performance of an intravascular ultrasound (IVUS) imaging system and, in particular, to a solid-state IVUS imaging system. In particular, the present disclosure discloses mounting the IVUS transducers and the flex circuit on a structural uni-body made of a polymeric substance injected or pre-doped with acoustic dampening material. The use of the polymeric substance, pre-doped with acoustic dampening material, allows for consistent sound absorption throughout the length of the uni-body and improves the signal-to-noise ratio associated with the IVUS signals, which optimizes the overall acoustic performance of the IVUS imaging system. Also, the use of the solid pre-doped polymeric substance to construct the uni-body eliminates the need to use any liquid backing material. As such, embodiments of the devices and systems proposed in the present disclosure avoid inconsistent and non-uniform acoustic performance that may be observed with respect to the conventional solid-state IVUS imaging systems. Further, embodiments of the presently disclosed devices and systems have improved manufacturability because there is no need to heat and cure any liquid backing material. The overall cost associated with manufacturing the solid-state IVUS system is also reduced.

FIG. 1 is a diagrammatic schematic view of an intravascular ultrasound (IVUS) imaging system 100 according to an embodiment of the present disclosure. In some embodiments, the IVUS imaging system 100 may be a piezoelectric zirconate transducer (PZT) solid-state IVUS imaging system. In other embodiments, the system 100 may incorporate capacitive micromachined ultrasonic transducers (CMUTs), and/or piezoelectric micromachined ultrasound transducers (PMUTs). The IVUS imaging system 100 may include an IVUS intravascular device 102, a patient interface module (PIM) 104, an IVUS console or processing system 106, and/or a monitor 108.

At a high level, the IVUS intravascular device 102 emits ultrasonic energy from transducers included in a scanner assembly 110 at a distal end of the imaging system 100. The ultrasonic energy is reflected by tissue structures surrounding the scanner 110 and the echo signals from the tissue may be received and amplified by circuitry included in the scanner 110. The PIM 104 may facilitate communication of signals between the IVUS console 106 and the IVUS intravascular device 102 to control the operation of the scanner assembly 110. This may include generating and/or providing control signals to configure the scanner and trigger the transmitter circuits and transferring echo signals captured by the scanner assembly 110 to the IUVS console 106. With regard to the echo signals, the PIM 104 may forward the received signals and, in some embodiments, may perform preliminary signal processing prior to forwarding the signals to the console 106. For example, the PIM 104 may perform amplification, filtering, and/or aggregating of the data prior to forwarding the signals to the console 106. In one embodiment, the PIM 104 may also supply high- and low-voltage DC power to support operation of the circuitry within the scanner 110. The IVUS console 106 may receive the echo data from the scanner 110 by way of the PIM 104 and may process the data to create an image of the tissue surrounding the scanner 110. The console 106 may also display the image on the monitor 108.

In some embodiments, the intravascular device includes some features similar to traditional solid-state intravascular devices, such as the EagleEye® catheter available from Volcano Corporation and those disclosed in U.S. Pat. No. 7,846,101, which is hereby incorporated by reference in its entirety. For example, the IVUS device 102 may include the ultrasound scanner assembly 110 at a distal end of the device 102 and a cable 112 extending along the longitudinal body of the device 102. The cable 112 may terminate in a connector 114 at a proximal end of the device 102. The connector 114 may electrically couple the cable 112 to the PIM 104 and may physically connect the IVUS device 102 to the PIM 104. In some embodiments, the IVUS device 102 may further include a guide wire exit port 116. Accordingly, in some instances the IVUS device may be a rapid-exchange catheter. The guide wire exit port 116 may allow a guide wire 118 to be inserted towards the distal end in order to direct the device 102 through a vessel 120. Vessel 120 may represent fluid filled or surrounded structures, both natural and man-made, within a living body that may be imaged and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to imaging natural structures, the images may also include imaging man-made structures such as, but without limitation, heart valves, stents, shunts, filters and other devices positioned within the body. In an embodiment, the IVUS device 102 may include an inflatable balloon portion 122 near the distal end. The balloon portion 122 may be open to a lumen that travels along the length of the IVUS device and ends in an inflation port (not shown). The balloon 122 may be selectively inflated or deflated via the inflation port.

FIG. 2 is a top view of a portion of an ultrasound scanner assembly 110 according to an embodiment of the present disclosure. FIG. 2 depicts the ultrasound scanner assembly 110 in its flat form. The scanner assembly 110 may include a transducer array 202 and transducer control circuits 204 (including controllers 204a and 204b) attached to a flex circuit 206. The transducer array 202 may include any number and type of ultrasound echo transducers 210, although for clarity only a limited number of ultrasound transducers are illustrated in FIG. 2. In some embodiments, the transducer array 202 may include 64 individual ultrasound transducers 210. In some embodiments, the transducer array 202 may include 32 ultrasound transducers. Other numbers are both contemplated and provided for. In some embodiments, the ultrasound transducers 210 of the transducer array 202 may be piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array may include piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In the illustrated embodiment, the scanner assembly 110 may include nine transducer control circuits 204, of which five are shown. Designs incorporating other numbers of transducer control circuits 204 including 4, 8, 9, 16, 17 and more may be utilized in other embodiments. In some embodiments, a single controller may be designated a master controller and maybe configured to receive signals directly from the cable 112. The remaining controllers may be slave controllers. In the depicted embodiment, the master controller 204a does not directly control any transducers 210. In other embodiments, the master controller 204a may have the same number of transducers 210 as the slave controllers 204b or may have a reduced set of transducers 210 as compared to the slave controllers 204b. In the illustrated embodiment, a single master controller 204a and eight slave controllers 204b are provided. Eight transducers may be assigned to each slave controller 204b. Such controllers may be referred to as 8-channel controllers based on the number of transducers they are capable of driving.

The master controller 204a may generate and/or provide respective control signals for the slave controllers 204b based on configuration data and transmit triggers received via the cable 112. The master controller 204a may also receive echo data from slave controllers 204b and retransmits the same over the cable 112. To do so, in some embodiments, the master controller 204a may include an echo amplifier (not shown). In this configuration, the master controller 204a may receive unamplified or partially amplified echo data and may perform the necessary amplification for driving the echo data along the cable 112.

In an embodiment, the flex circuit 206 may provide structural support and may physically and electrically connect the transducer control circuits 204 to the respective transducers 210. The flex circuit 206 may contain a film layer of a flexible polyimide material such as KAPTON™ (trademark of DuPont). Other suitable materials include polyester films, polyimide films, polyethylene napthalate films, or polyetherimide films, and other flexible printed circuit substrates as well as products such as Upilex® (registered trademark of Ube Industries) and TEFLON® (registered trademark of E.I. du Pont). In accordance with the present disclosure, the film layer may be configured to be wrapped around a uni-body structure to form a cylindrical toroid in some instances. Therefore, the thickness of the film layer may be generally related to the degree of curvature in the scanner assembly 110. In some embodiments, the film layer may be between 5 μm and 100 μm, with some particular embodiments being between 12.7 μm and 25.1 μm.

In some embodiments, the flex circuit 206 may further include conductive electrical traces formed on the film layer. These conductive traces may carry signals between the transducer control circuits 204 and the transducers 210, and may provide a set of pads for connecting the conductors of the cable 112. Suitable materials for the conductive traces include copper, gold, aluminum, silver, tantalum, nickel, and tin and may be deposited on the flex circuit 206 by processes such as sputtering, plating, and etching. In some embodiments, the flex circuit 206 may include a chromium adhesion layer. The width and thickness of the conductive traces may be selected to provide proper conductivity and resilience when the flex circuit 206 is rolled to form the toroid. In that regard, an exemplary range for the thickness of a conductive trace 210 may be between 10-50 μm. For example, in an embodiment, 20 μm conductive traces 210 may be separated by 20 μm of space. The width of a conductive trace 210 may be further determined by the size of a pad of a device or the width of a wire to be coupled to the trace.

As the circuit may be rolled to form the finished scanner assembly, the control circuits 204, including both master and slave controllers, may be shaped accordingly. This may include a control circuit 204 edge configured to interface with an edge of an adjacent control circuit 204. In some embodiments, the control circuits 204 that may include interlocking teeth 212a and 212b. For example, control circuits 204 may be formed with a recess and projection 212a that interlocks with a recess and projection 212b of an adjacent control circuit 204 to form a box joint or finger joint. In some embodiments, a control circuit 204 may include a chamfered edge 214, either alone or in combination with a recess and projection. The chamfered edge 214 may be configured to abut an edge of an adjacent control circuit 204. In some such embodiments, the edge of the adjacent controller may be chamfered as well. In some embodiments, each of the controllers 204 may interlock with two adjacent controllers utilizing a similar recess and projection interface.

FIG. 3 illustrates an exemplary mounting structure 300 according to an embodiment of the present disclosure. The mounting structure 300 may include a ferrule 301 at least partially surrounded by a solid uni-body 302. In one embodiment, the ferrule 301 may have a cylindrical shape. However, other shapes of the ferrule 301 are also contemplated including geometrical, non-geometrical, symmetrical, non-symmetrical, cross-sectional profiles. The ferrule 301 may be formed of a metallic or a non-metallic substance. A lumen region 303 inside the ferrule 301 may be open and in communication with the guide wire exit port 116 and thereby allow the scanner assembly 110 and the associated intravascular device to advance over a guide wire. In some embodiments, the uni-body 302 has a cylindrical shape to conform to the cylindrical shape of the scanner assembly 110. The uni-body 302 may be made of a polymeric substance injected or pre-doped with acoustic dampening material. The polymer substance may be Nylon, Pebax, PE, Kapton, PTFE, PVDF, Polycarbonate, Peek, PET ETFE, or any other type of extruded or molded tubing. The acoustic dampening material may be any type of a conductive adhesive, such as epoxy. In some embodiments, the flex circuit 206 may be attached or mounted on the mounting structure 300. For example, the flex circuit 206 may be mounted on the uni-body 302 by wrapping the flex circuit 206 in a rolled configuration around the uni-body 302. Additionally or optionally, the flex circuit 206, including the transducer array 202, may be fixedly secured to the outer surface of the uni-body 302 with an adhesive to further limit any reverberations or acoustic disturbances. The uni-body 302 may be a solid structure made of the polymeric substance that is able to adequately support the flex circuit 206 and the connected transducer array 202. The use of a polymeric substance, uniformly doped with acoustic dampening material, allows for consistent sound absorption throughout the length of the uni-body 302. This improves the signal-to-noise ratio associated with the ultrasound pulses and echo signals provided by the transducers 210, thereby optimizing the overall acoustic performance of the IVUS imaging system.

In some embodiments, the uni-body 302 may be fabricated by swaging the pre-doped polymeric material through a hollow cylindrical die. In some embodiments, a mold of the desired shape of the uni-body 302 may be designed and the pre-doped polymeric substance may be injected into the mold. In some embodiments, the uni-body 302 may be fabricated by using an extrusion process to create a structure having a desired cross-sectional profile. Additional processing, such as cutting, completing, grinding, tapering, texturing, etc. may be performed on the molded, swaged, and/or extruded structures to define the uni-body 301.

FIG. 4 illustrates another exemplary mounting structure 400 according to an embodiment of the present disclosure. In the illustrated embodiment, the uni-body 302 may include a plurality of radiopaque markers 410. In some embodiments, the polymeric material of the uni-body is doped and/or coated with radiopaque material to form the radiopaque markers 410 at desired positions on the uni-body. In another embodiment, the radiopaque markers 410 may be separate elements such as circumferential bands securely affixed on the outer surface of the uni-body 302. The radiopaque markers 410 may be formed of one or more radiopaque materials including, but not limited to, gold, tungsten, iridium, rhodium, platinum, barium, bismuth, and combinations and/or alloys thereof. In one embodiment, the uni-body 302 may include the plurality of radiopaque markers on a portion covered by the flex circuit 206 and the transducers 210. In another embodiment, the uni-body 302 may include the plurality of radiopaque markers along a majority or an entire length of the uni-body 302. The plurality of radiopaque markers may be of equal or variable size and may be placed equidistantly or variably on the uni-body 302. In one embodiment, a width of a radiopaque marker may be substantially equal to or proportional to a distance between two adjacent radiopaque markers. It is advantageous to include the plurality of radiopaque markers on the portion covered by the flex circuit 206 and the transducers 210 to enable the operator to accurately observe and track the position of the transducers 210 once the IVUS device 102 is inserted in the body of the patient. The knowledge of the accurate position of the transducers 210 allows accurate placement of the transducers 210 in the desired locations within the vessel of interest for imaging. This can reduce instances in which an operator is required to guess or estimate the location of the transducers 210 inside the device 102 during the imaging procedure. As such, the overall efficiency of the imaging procedure is increased. The radiopaque markers can also be utilized to track the position of the intravascular device and/or the transducer to facilitate co-registration of the images obtained with the intravascular device to other types of intravascular or extra-vascularly obtained patient data.

FIG. 5 illustrates a cross-sectional view of the transducer region 500 of the scanner assembly 110 according to an embodiment of the present disclosure. In the illustrated embodiment, the transducer region 500 is depicted in its rolled form. In that regard, in some instances the scanner is transitioned from a flat configuration to a rolled or more cylindrical configuration. For example, in some embodiments, techniques are utilized as disclosed in one or more of U.S. Pat. No. 6,776,763, titled "ULTRASONIC TRANSDUCER ARRAY AND METHOD OF MANUFACTURING THE SAME and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As the name implies, the transducer region 500 of the scanner contains the transducers 210 that are attached to the flex circuit 206, and in particular, to the traces of the flex circuit 206. In the illustrated embodiment, the flex circuit 206 also includes a conductive ground layer 502 and an outer membrane 504 used to insulate and cover the ground layer 502 and to protect the scanner 110 from the environment. Insulator materials for the outer membrane 504 may be selected for their biocompatibility, durability, hydrophilic or hydrophobic properties, low-friction properties, ultrasonic permeability, and/or other suitable criteria. For example, the outer membrane may include Parylene™ (trademark of Union Carbide). Other suitable materials include heat shrink tubing such as polyester or PVDF, a melt-formable layers such as Pebax® (registered trademark of Arkema) or polyethylene, and/or other suitable membrane materials. As can be seen, the size, shape, and spacing of the ultrasound transducers 210 at least partially define the shape of the transducer region 500. In embodiments with 64 ultrasound transducers 210, the cross-section 500 of the transducer region may be circular or substantially circular, as shown.

FIG. 6 illustrates a cross-sectional view of a control region 600 of an ultrasound scanner assembly 110 according to an embodiment of the present disclosure. The control region 600 may include nine (9) transducer control circuits 204 connected to the flex circuit 206. In some embodiments, the control circuits 204 may include respective contact bumps 602 to couple the control circuits to the respective traces of the flex 206. During formation, the contact may be heated, causing the solder to flow and join the metal core of a contact bump 602 to a trace of the flex circuit 206. An underfill material 604 may be applied between the control circuits 204 and the flex circuit 206 to increase the bond strength and to provide structural support for the control region. The underfill material 604 may also insulate conductive structures including the contact bumps 602 and promote thermal conduction. Because portions of the flex circuit 206 adjacent to the transducer control circuits 204 are flat, utilizing narrower and more numerous transducer control circuits 204 in place of fewer but larger control circuits produces a more circular cross-section. It follows that designs utilizing 8, 9, 16, or more transducer control circuits 204 will have a more circular cross-section than designs with 4 or 5 transducer control circuits 204. This has the advantage of reducing the effective diameter 608 of the scanner assembly 110. Further, because narrower transducer control circuits 204 may be used, the length of the non-flexible control region 600 along the longitudinal axis of the device 102 may be decreased.

In addition, utilizing narrower and more numerous transducer control circuits 204 to produce a more circular cross-section is advantageous because it allows for a shorter transition zone. FIG. 7 illustrates a perspective view of a portion of an exemplary ultrasound scanner assembly 110 according to an embodiment of the present disclosure. The scanner assembly 110 may include a ferrule 701 and a uni-body 702. The uni-body 702 may include a transducer region 500, a control region 600, and a transition zone 700. In some embodiments, the form or shape of the control region 600 may be based on the number of transducer control circuits 204 to be accommodated. For example, in one embodiment, the shape of the control region 600 may resemble a square to accommodate four (4) transducer control circuits 204. In some embodiments, the shape of the control region 600 may resemble an octagon to accommodate eight (8) transducer control circuits 204. In some embodiments, nine (9) transducer control circuits 204 are designed to be accommodated and the shape of the control region 600 may resemble a nonagon, as illustrated in FIG. 6.

The transition zone 700 may be located between the transducer region 500 and the control region 600. In contrast to the transducer region 500 and the control region 600, the transition zone 700 is free of rigid structures. The cross-sectional shape of the transition zone 700 is defined by the adjacent regions 500 and 600 in some instances. Generally, the cross-sectional shape of the transition zone 700 transitions between that of the transducer region 500 and that of the control region 600. The transition zone 700 may be used to reduce sharp angles that can stress the flex circuit 206 and/or the conductive traces. Because of the more circular cross-section of the associated control region 600 proposed in the present disclosure, embodiments utilizing, for example, 8, 9, 16, or more transducer control circuits 204 support a shorter transition zone 700. In other words, because both transducer control circuits 204 and ultrasound transducers 210 produce flat areas within the flex circuit 206, substituting physically narrower devices reduces the non-circular regions of the flex circuit 206 caused by each individual device. Therefore, a design utilizing, for example, nine (9) transducer control circuits has a more circular control region 600 with respect to a design utilizing four (4) transducer control circuits 204 and likewise accommodates a shorter transition zone 700. In an exemplary embodiment with four (4) control circuits 204, the transition zone 700 is approximately 1 to 1.5 catheter diameters in order to transition from a substantially square shape to a substantially circular shape. This works out to be between 1000 and 1500 μm for a 3Fr catheter. In contrast, with the implementation of nine (9) control circuits 204, the transition zone 700 is approximately 0.5 to 0.75 catheter diameters, or between 500 μm and 750 μm for a 3Fr catheter. In this way, designs incorporating narrower and more numerous transducer control circuits 204 may produce a shorter scanner assembly 110. Because the scanner assembly 110 may be typically inflexible or rigid compared to the surrounding portion of the device, reducing the length of the assembly 110 results in a more agile IVUS device capable of maneuvering through complex vascular branches and producing less discomfort to the patient.

As discussed above, the uni-body 702 may be fabricated by any one or more of swaging, using a mold, and/or the extrusion processes such that each of the transducer region 500, the control region 600, and/or the transition zone 700 have the desired cross-sectional profiles. In that regard, two or more of the transducer region 500, the control region 600, and the transition zone 700 may be formed separately and then joined together (e.g., using an adhesive or other suitable coupling mechanism). Alternatively, the transducer region 500, the control region 600, and the transition zone 700 may be integrally formed as a single component via the swaging, molding, and/or the extrusion processes.

FIG. 8 illustrates an exemplary method to provide the scanner assembly 110 according to an embodiment of the present disclosure. The method starts at step 800. At step 801, polymeric material doped with acoustic dampening material is provided. Additionally or optionally, the polymeric material may include radiopaque markers as discussed above. At step 802, the uni-body is fabricated using the doped polymeric material. In some embodiments, the uni-body may be fabricated using the previously discussed swaging, injection molding, and/or the extrusion processes. In some embodiments, the uni-body may be attached to a ferrule. For example, the uni-body may at least partially surround the ferrule, as shown in FIG. 3. At step 803, the flex circuit connected to the transducers is mounted onto the fabricated uni-body. At step 804, the flex circuit is fixedly secured to the uni-body using an adhesive. At step 805, the uni-body with the flex circuit is incorporated into the distal portion of an intravascular device. In some embodiments, the uni-body along with the flex circuit are included as part of a scanner assembly 110 of the intravascular device. The method ends at step 806.

It should be appreciated that while the exemplary embodiment is described in terms of an IVUS device, the present disclosure is not so limited. Thus, for example, other invasive medical devices such as, by way of non-limiting example, catheters, guidewires, and probes, having one or more sensing elements may utilize a similar approach to the mount the sensing element(s) and/or associated control circuitry. For example, in some instances pressure-sensing and/or flow-sensing intravascular devices utilize a similar approach in accordance with the present disclosure.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) device, comprising:
   a scanner assembly including:
      a mounting structure including:
         a ferrule including a lumen region, wherein the ferrule comprises a first diameter along an entire length;
         a polymeric substance surrounding a portion of the ferrule, wherein the polymeric substance is doped with acoustic damping material, wherein the polymeric substance comprises a cylindrical outer profile, wherein the cylindrical outer profile is defined by a constant thickness from a proximal end of the polymeric substance to a distal end of the polymeric substance; and
      a flex circuit comprising a plurality of controllers and a transducer array, wherein the flex circuit is mounted onto the cylindrical outer profile of the polymeric substance from the proximal end to the distal end such that the polymeric substance is disposed between the plurality of controllers and the ferrule.

2. The IVUS device of claim 1, wherein the ferrule and the polymeric substance are cylindrical in shape.

3. The IVUS device of claim 1, wherein the ferrule is made of a metallic substance.

4. The IVUS device of claim 1, wherein the ferrule is made of a polymer substance.

5. The IVUS device of claim 1, wherein the lumen region of the ferrule is sized and shaped to receive a guide wire.

6. The IVUS device of claim 1, wherein the acoustic damping material is a conductive adhesive.

7. The IVUS device of claim 1, wherein the polymeric substance is uniformly doped with the acoustic damping material.

8. The IVUS device of claim 1, wherein the flex circuit is mounted onto the polymeric substance by wrapping the flex circuit around the polymeric sub stance.

9. The IVUS device of claim 8, wherein the flex circuit is fixedly secured to the polymeric substance with an adhesive.

10. The IVUS device of claim 1, wherein the polymeric substance includes a plurality of radiopaque markers.

11. The IVUS device of claim 10, wherein the plurality of radiopaque markers includes separate elements fixedly secured to an outer surface of the polymeric substance.

12. The IVUS device of claim 10, wherein the polymeric substance is doped with a radiopaque material to form the plurality of radiopaque markers.

13. The IVUS device of claim 10, wherein the polymeric substance includes at least one of the plurality of radiopaque markers on a portion of the polymeric substance covered by the flex circuit.

14. The IVUS device of claim 1, wherein the scanner assembly includes a control region comprising the plurality of controllers, a transducer region comprising the transducer array, and a transition zone, wherein:
   the control region comprises a non-circular cross-sectional profile;
   the transducer region comprises a circular cross-sectional profile; and
   the transition zone comprises a cross-sectional profile that transitions from the non-circular cross-sectional profile to the circular cross-sectional profile.

15. The IVUS device of claim 1, wherein the polymeric substance comprises a solid cross-section from the proximal end of the polymeric substance to the distal end of the polymeric substance.

16. The IVUS device of claim 1, wherein the polymeric substance comprises a continuous outer surface extending longitudinally from the proximal end of the polymeric substance to the distal end of the polymeric substance, wherein the flex circuit is mounted onto the continuous outer surface.

17. The IVUS device of claim 1, wherein that the flex circuit is supported only by the polymeric substance doped with the acoustic damping material.

18. The IVUS device of claim 1, wherein a distal end of the ferrule is distal of the distal end of the polymeric substance and a proximal end of the ferrule is proximal of the proximal end of the polymeric substance such that the ferrule extends on either side of the polymeric substance.

19. The IVUS device of claim 1, wherein the flex circuit comprises a flexible substrate, wherein the plurality of controllers and the transducer array are coupled to the flexible substrate, wherein the flexible substrate is mounted onto the cylindrical outer profile of the polymeric substance from the proximal end to the distal end.

20. The IVUS device of claim 19, further comprising a ground layer surrounding and in contact with the flexible substrate, and an outer membrane surrounding and in contact with the ground layer, such that the outer membrane forms an outer surface of the scanner assembly.

\* \* \* \* \*